(12) United States Patent
Luria et al.

(10) Patent No.: US 10,398,295 B2
(45) Date of Patent: Sep. 3, 2019

(54) BALLOON ENDOSCOPE REPROCESSING SYSTEM AND METHOD

(71) Applicant: SMART MEDICAL SYSTEMS LTD., Ra'anana (IL)

(72) Inventors: Gilad Luria, Givataim (IL); Sagi Peled, Hadera (IL); Gad Terliuc, Raanana (IL)

(73) Assignee: SMART MEDICAL SYSTEMS LTD., Raanana (IL)

( * ) Notice: Subject to any disclaimer, the term of this patent is extended or adjusted under 35 U.S.C. 154(b) by 82 days.

(21) Appl. No.: 15/537,436

(22) PCT Filed: Nov. 26, 2015

(86) PCT No.: PCT/IL2015/051149
§ 371 (c)(1),
(2) Date: Jun. 19, 2017

(87) PCT Pub. No.: WO2016/103247
PCT Pub. Date: Jun. 30, 2016

(65) Prior Publication Data
US 2018/0140175 A1 May 24, 2018

Related U.S. Application Data

(60) Provisional application No. 62/124,551, filed on Dec. 22, 2014.

(51) Int. Cl.
*A61B 1/00* (2006.01)
*A61B 1/12* (2006.01)
(Continued)

(52) U.S. Cl.
CPC .......... *A61B 1/123* (2013.01); *A61B 1/00082* (2013.01); *A61B 1/125* (2013.01);
(Continued)

(58) Field of Classification Search
CPC ......... A61B 1/00; A61B 1/00082; A61B 1/12; A61B 1/123; A61B 1/125; A61B 1/31;
(Continued)

(56) References Cited

U.S. PATENT DOCUMENTS

| 3,837,347 A | 9/1974 | Tower |
| 3,895,637 A | 7/1975 | Choy |

(Continued)

FOREIGN PATENT DOCUMENTS

| CA | 2661242 | 10/2010 |
| CN | 1394543 | 2/2003 |

(Continued)

OTHER PUBLICATIONS

An International Search Report and a Written Opinion both dated Sep. 4, 2014, which issued during the prosecution of Applicant's PCT/IL2014/000025.

(Continued)

*Primary Examiner* — Nguyen Q. Ha
(74) *Attorney, Agent, or Firm* — Alphapatent Associates, Ltd; Daniel J. Swirsky

(57) ABSTRACT

A reprocessing method for balloon endoscopes, the method including introducing a balloon endoscope to be reprocessed into an endoscope reprocessing system, performing reprocessing on the balloon endoscope to be reprocessed while a balloon of the balloon endoscope is deflated, thereafter inflating the balloon of the balloon endoscope, thereafter deflating the balloon of the balloon endoscope and thereafter performing further reprocessing on the balloon endoscope to be reprocessed while the balloon of the balloon endoscope is deflated.

19 Claims, 7 Drawing Sheets

(51) Int. Cl.
*A61B 1/31* (2006.01)
*B08B 3/00* (2006.01)
*G01M 3/32* (2006.01)
*A61M 25/10* (2013.01)
*A61B 90/70* (2016.01)
*B08B 3/10* (2006.01)

(52) U.S. Cl.
CPC ...... *A61M 25/1018* (2013.01); *G01M 3/3218* (2013.01); *A61B 2090/701* (2016.02); *B08B 3/10* (2013.01); *B08B 2203/007* (2013.01)

(58) Field of Classification Search
CPC .. A61B 2090/701; A61F 2/958; A61M 25/10; A61M 25/1018; B08B 3/00; B08B 3/10; B08B 2203/007; G01M 3/00; G01M 3/3218
See application file for complete search history.

(56) References Cited

U.S. PATENT DOCUMENTS

| | | | |
|---|---|---|---|
| 4,040,413 A | 8/1977 | Ohshiro | |
| 4,148,307 A | 4/1979 | Utsugi | |
| 4,176,662 A | 12/1979 | Frazer | |
| 4,195,637 A | 4/1980 | Gruntzig et al. | |
| 4,224,929 A | 9/1980 | Furihata | |
| 4,261,339 A | 4/1981 | Hanson et al. | |
| 4,453,545 A | 6/1984 | Inoue | |
| 4,616,652 A | 10/1986 | Simpson | |
| 4,676,228 A | 6/1987 | Krasner et al. | |
| 4,681,093 A | 7/1987 | Ono et al. | |
| 4,690,131 A | 9/1987 | Lyddy et al. | |
| 4,721,123 A | 1/1988 | Cosentino et al. | |
| 4,862,874 A | 9/1989 | Kellner | |
| 4,917,088 A | 4/1990 | Crittenden | |
| 5,135,487 A | 8/1992 | Morrill et al. | |
| 5,259,366 A | 11/1993 | Reydel et al. | |
| 5,310,524 A | 5/1994 | Campbell et al. | |
| 5,338,299 A | 8/1994 | Barlow | |
| 5,411,016 A | 5/1995 | Kume et al. | |
| 5,454,364 A | 10/1995 | Kruger | |
| 5,569,220 A | 10/1996 | Webster, Jr. | |
| 5,593,419 A | 1/1997 | Segar | |
| 5,599,301 A | 2/1997 | Jacobs et al. | |
| 5,607,441 A | 3/1997 | Sierocuk et al. | |
| 5,653,240 A | 8/1997 | Zimmon | |
| 5,693,014 A | 12/1997 | Abele | |
| 5,700,242 A | 12/1997 | Mulder | |
| 5,707,382 A | 1/1998 | Sierocuk et al. | |
| 5,707,392 A | 1/1998 | Kortenbach | |
| 5,823,940 A | 10/1998 | Newman | |
| 5,904,701 A | 5/1999 | Daneshvar | |
| 5,984,860 A | 11/1999 | Shan | |
| 6,007,482 A | 12/1999 | Madni et al. | |
| 6,162,171 A | 12/2000 | Ng et al. | |
| 6,261,260 B1 | 7/2001 | Maki et al. | |
| 6,412,334 B1 | 7/2002 | Kral et al. | |
| 6,461,294 B1 | 10/2002 | Oneda et al. | |
| 6,585,639 B1 | 7/2003 | Kotmel et al. | |
| 6,589,208 B2 | 7/2003 | Ewers et al. | |
| 6,663,589 B1 | 12/2003 | Halevy | |
| 6,695,810 B2 | 2/2004 | Peacock | |
| 6,702,735 B2 | 3/2004 | Kelly | |
| 6,764,441 B2 | 7/2004 | Chiel | |
| 6,986,736 B2 | 1/2006 | Williams et al. | |
| 7,081,096 B2 | 7/2006 | Brister et al. | |
| 7,169,140 B1 | 1/2007 | Kume | |
| 7,635,346 B2 | 12/2009 | Cabiri et al. | |
| 7,695,428 B2 | 4/2010 | Machida | |
| 7,699,771 B2 | 4/2010 | Wendlandt | |
| 7,713,191 B2 | 5/2010 | Sekiguchi et al. | |
| 7,837,672 B2 | 11/2010 | Intoccia | |
| 7,887,480 B2 | 2/2011 | Sekiguchi | |
| 7,918,788 B2 | 4/2011 | Lin et al. | |
| 7,963,911 B2 | 6/2011 | Turliuc | |
| 8,002,698 B2 | 8/2011 | Motai | |
| 8,012,084 B2 | 9/2011 | Machida | |
| 8,152,715 B2 | 4/2012 | Root et al. | |
| 8,187,221 B2 | 5/2012 | Bates | |
| 8,197,463 B2 | 6/2012 | Intoccia | |
| 8,273,013 B2 | 9/2012 | Niwa et al. | |
| 8,419,678 B2 | 4/2013 | Cabiri et al. | |
| 8,480,572 B2 | 7/2013 | Takakazu | |
| 8,545,382 B2 | 10/2013 | Suzuki et al. | |
| 8,727,970 B2 | 5/2014 | Terliuc et al. | |
| 8,939,895 B2 | 1/2015 | Simchony | |
| 9,119,532 B2 | 9/2015 | Terliuc et al. | |
| 9,511,209 B2 | 1/2016 | Drasler | |
| 9,278,202 B2 | 3/2016 | Ranade | |
| 9,427,142 B2 | 8/2016 | Terliuc et al. | |
| 9,480,390 B2 | 11/2016 | Farhadi | |
| 9,521,945 B2 | 12/2016 | Farhadi | |
| 9,596,979 B2 | 3/2017 | Terliuc et al. | |
| 9,604,042 B2 | 3/2017 | Fox | |
| 9,661,994 B2 | 5/2017 | Terliuc et al. | |
| 9,795,280 B2 * | 10/2017 | Ueda | A61B 1/121 |
| 2001/0032494 A1 | 10/2001 | Greszler | |
| 2002/0147385 A1 | 10/2002 | Butler et al. | |
| 2003/0074015 A1 | 4/2003 | Nakao | |
| 2003/0236495 A1 | 12/2003 | Kennedy | |
| 2004/0102681 A1 | 5/2004 | Gross | |
| 2004/0210116 A1 | 10/2004 | Nakao | |
| 2004/0236366 A1 | 11/2004 | Kennedy et al. | |
| 2005/0027253 A1 | 2/2005 | Castellano et al. | |
| 2005/0124856 A1 | 6/2005 | Fujikura et al. | |
| 2005/0125005 A1 | 6/2005 | Fujikura | |
| 2005/0133453 A1 | 6/2005 | Woodruff et al. | |
| 2005/0137457 A1 | 6/2005 | Machida | |
| 2005/0159702 A1 | 7/2005 | Sekiguchi et al. | |
| 2005/0165233 A1 | 7/2005 | Hamedi et al. | |
| 2005/0165273 A1 | 7/2005 | Takano | |
| 2005/0171400 A1 | 8/2005 | Itoi | |
| 2006/0095063 A1 | 5/2006 | Sekiguchi | |
| 2006/0100480 A1 | 5/2006 | Ewers et al. | |
| 2006/0111610 A1 | 5/2006 | Machida | |
| 2006/0116549 A1 | 6/2006 | Sekiguchi et al. | |
| 2006/0161044 A1 | 7/2006 | Oneda et al. | |
| 2006/0282088 A1 | 12/2006 | Ryan | |
| 2007/0010785 A1 | 1/2007 | Sekiguchi et al. | |
| 2007/0038026 A1 | 2/2007 | Yoshida et al. | |
| 2007/0083158 A1 | 4/2007 | Hirszowicz et al. | |
| 2007/0185385 A1 | 8/2007 | Noguchi | |
| 2007/0191678 A1 | 8/2007 | Sekiguchi | |
| 2007/0213586 A1 | 9/2007 | Kenji | |
| 2007/0244361 A1 | 10/2007 | Ikeda et al. | |
| 2007/0270645 A1 | 11/2007 | Ikeda | |
| 2007/0276181 A1 | 11/2007 | Terliuc | |
| 2008/0009673 A1 | 1/2008 | Khachi | |
| 2008/0161645 A1 | 7/2008 | Goldwasser et al. | |
| 2008/0177142 A1 | 7/2008 | Roskopf | |
| 2008/0200759 A1 | 8/2008 | Niwa et al. | |
| 2008/0306441 A1 | 12/2008 | Brown et al. | |
| 2009/0012469 A1 | 1/2009 | Nita | |
| 2009/0018500 A1 | 1/2009 | Carter et al. | |
| 2009/0048483 A1 | 2/2009 | Yamamoto | |
| 2009/0156896 A1 | 6/2009 | Kura | |
| 2009/0187069 A1 | 7/2009 | Terliuc et al. | |
| 2009/0234188 A1 | 9/2009 | Matsuura et al. | |
| 2009/0287058 A1 | 11/2009 | Terliuc | |
| 2010/0041951 A1 | 2/2010 | Glozman et al. | |
| 2010/0042046 A1 | 2/2010 | Chang et al. | |
| 2010/0217185 A1 | 8/2010 | Terliuc et al. | |
| 2012/0178994 A1 | 7/2012 | Schembre | |
| 2012/0232342 A1 | 9/2012 | Reydel | |
| 2012/0285488 A1 | 11/2012 | Labib et al. | |
| 2013/0023920 A1 | 1/2013 | Terliuc et al. | |
| 2013/0090527 A1 | 4/2013 | Axon | |
| 2013/0116549 A1 | 5/2013 | Gunday | |
| 2014/0088362 A1 | 3/2014 | Terliuc et al. | |
| 2014/0155696 A1 | 6/2014 | Sakata | |
| 2015/0073216 A1 | 3/2015 | Papay | |
| 2015/0273191 A1 | 10/2015 | Terliuc et al. | |
| 2015/0335229 A1 | 11/2015 | Terliuc | |

(56) References Cited

U.S. PATENT DOCUMENTS

| | | | |
|---|---|---|---|
| 2016/0022120 A1 | 1/2016 | Terliuc et al. | |
| 2016/0081536 A1 | 3/2016 | Farhadi | |
| 2016/0089001 A1 | 3/2016 | Hara et al. | |
| 2016/0095508 A1* | 4/2016 | Terliuc | A61B 1/00082 134/18 |
| 2017/0014099 A1* | 1/2017 | Morimoto | A61B 8/4416 |
| 2017/0027415 A1 | 2/2017 | Terliuc et al. | |
| 2017/0027433 A1 | 2/2017 | Terliuc | |
| 2017/0065155 A1 | 3/2017 | Farhadi | |
| 2017/0216568 A1 | 3/2017 | Terliuc et al. | |
| 2017/0100017 A1 | 4/2017 | Terliuc et al. | |
| 2017/0106173 A1 | 4/2017 | Chanduszko | |
| 2017/0203080 A1 | 7/2017 | Terliuc et al. | |
| 2017/0360282 A1 | 12/2017 | Terliuc et al. | |
| 2018/0084973 A1 | 3/2018 | Terliuc et al. | |
| 2018/0333043 A1 | 11/2018 | Terliuc et al. | |

FOREIGN PATENT DOCUMENTS

| | | |
|---|---|---|
| CN | 2624936 | 7/2004 |
| CN | 1550203 | 12/2004 |
| CN | 1636502 | 7/2005 |
| CN | 1647747 | 8/2005 |
| CN | 1649630 | 8/2005 |
| CN | 1827031 | 9/2006 |
| CN | 1917802 | 2/2007 |
| CN | 1933766 | 3/2007 |
| CN | 1946328 | 4/2007 |
| CN | 1951312 | 4/2007 |
| CN | 1964665 | 5/2007 |
| CN | 101015440 | 8/2007 |
| CN | 101103898 | 1/2008 |
| CN | 101243965 | 8/2008 |
| CN | 101347321 | 1/2009 |
| CN | 101380220 | 3/2009 |
| CN | 101396256 | 4/2009 |
| CN | 101522091 | 9/2009 |
| CN | 101541227 | 9/2009 |
| CN | 101664560 | 3/2010 |
| CN | 102791180 | 11/2012 |
| CN | 103269638 | 8/2013 |
| DE | 4317601 A1 | 12/1994 |
| DE | 10209993 A1 | 4/2003 |
| EP | 0 212 696 | 3/1987 |
| EP | 0473045 A1 | 3/1992 |
| EP | 0733342 | 9/1996 |
| EP | 1433410 | 6/2004 |
| EP | 1547641 | 6/2005 |
| EP | 1550465 A1 | 7/2005 |
| EP | 1656879 | 5/2006 |
| EP | 1666864 A1 | 6/2006 |
| EP | 1707221 A1 | 10/2006 |
| EP | 1556118 B1 | 12/2006 |
| EP | 2108303 A1 | 10/2009 |
| EP | 1726248 B1 | 12/2010 |
| EP | 1335659 B1 | 4/2011 |
| EP | 1551316 B1 | 8/2011 |
| EP | 2110068 B1 | 8/2011 |
| EP | 2764818 A1 | 8/2014 |
| EP | 1706169 B1 | 5/2015 |
| EP | 2320984 B1 | 10/2015 |
| JP | S48-068542 | 6/1973 |
| JP | SHO50-016762 | 2/1975 |
| JP | S57-57804 | 4/1982 |
| JP | S62-002925 | 6/1985 |
| JP | SHO61-284226 | 12/1986 |
| JP | SHO62-002925 | 1/1987 |
| JP | S61-202274 | 7/1988 |
| JP | SHO63-102429 | 7/1988 |
| JP | SHO64-017203 | 1/1989 |
| JP | H2-58402 | 4/1990 |
| JP | H04-102436 | 4/1992 |
| JP | H04-297219 | 10/1992 |
| JP | HEI 05337081 | 12/1993 |
| JP | H06-63045 | 3/1994 |
| JP | HEI6-339455 | 12/1994 |
| JP | HEI7-12101 | 2/1995 |
| JP | HEI7-148105 | 6/1995 |
| JP | H08228996 | 9/1996 |
| JP | HEI10-127571 | 5/1998 |
| JP | HEI10-286309 | 10/1998 |
| JP | HEI11-225947 | 8/1999 |
| JP | 2000-060793 | 2/2000 |
| JP | 2000-329534 | 11/2000 |
| JP | 2002-34900 | 2/2002 |
| JP | 2002-301019 | 10/2002 |
| JP | 2003-275173 | 9/2003 |
| JP | 2003250896 | 9/2003 |
| JP | 2004-97718 | 4/2004 |
| JP | 2004-329720 | 11/2004 |
| JP | 2005-185704 | 7/2005 |
| JP | 2005-185706 | 7/2005 |
| JP | 2005-185707 | 7/2005 |
| JP | 2005-279128 | 10/2005 |
| JP | 2005296256 | 10/2005 |
| JP | 2005-334475 | 12/2005 |
| JP | 2006-130014 | 5/2006 |
| JP | 2006-167310 | 6/2006 |
| JP | 2006-304906 | 11/2006 |
| JP | 2006-334149 | 12/2006 |
| JP | 2007-014475 | 1/2007 |
| JP | 2007-026814 | 2/2007 |
| JP | 2007-130082 | 5/2007 |
| JP | 2007-517576 | 7/2007 |
| JP | 2007-521907 | 8/2007 |
| JP | 2007-268137 | 10/2007 |
| JP | 2007-268147 | 10/2007 |
| JP | 2007-296054 | 11/2007 |
| JP | 2008-006000 | 1/2008 |
| JP | 2008125886 | 6/2008 |
| JP | 2008-537493 | 9/2008 |
| JP | 2009-056121 | 3/2009 |
| JP | 2009-195321 | 9/2009 |
| JP | 2009-537212 | 10/2009 |
| JP | 2009-254554 | 11/2009 |
| JP | 2012504431 | 4/2010 |
| WO | 96/00099 | 1/1996 |
| WO | 98/30249 | 7/1998 |
| WO | 02/094087 | 11/2002 |
| WO | 2005/017854 | 2/2005 |
| WO | 2005/074377 | 8/2005 |
| WO | 2005/089625 | 9/2005 |
| WO | WO2006123590 A1 | 11/2006 |
| WO | 2007/023492 | 3/2007 |
| WO | 2007/135665 | 11/2007 |
| WO | 2008/004228 | 1/2008 |
| WO | WO2008073126 A1 | 6/2008 |
| WO | WO2008121143 A1 | 10/2008 |
| WO | 2008/142685 | 11/2008 |
| WO | 2009/122395 | 10/2009 |
| WO | 2010/046891 | 4/2010 |
| WO | WO2010070291 A2 | 6/2010 |
| WO | 2010/137025 | 12/2010 |
| WO | 2011/111040 | 9/2011 |
| WO | 2011111040 A2 | 9/2011 |
| WO | 2012120492 A1 | 9/2012 |
| WO | 2014068569 A2 | 5/2014 |
| WO | 2014/188402 | 11/2014 |
| WO | 2014188402 A1 | 11/2014 |
| WO | WO2014188402 A1 | 11/2014 |
| WO | WO2015160970 A1 | 10/2015 |
| WO | WO2016103247 A1 | 6/2016 |
| WO | WO2017004432 A1 | 1/2017 |

OTHER PUBLICATIONS

An International Preliminary Report on Patentability dated Nov. 24, 2015, which issued during the prosecution of Applicant's PCT/IL2014/000025.

European Search Report dated Jan. 4, 2017, which issued during the prosecution of Applicant's European App No. 14800390.8.

(56) References Cited

OTHER PUBLICATIONS

An Office Action dated Dec. 9, 2016, which issued during the prosecution of Chinese Patent Application No. 201480029252.5.
European Search Report dated Apr. 8, 2014, which issued during the prosecution of Applicant's App No. 11752941.2.
An Office Action dated May 25, 2016, which issued during the prosecution of Chinese Patent Application No. 201410483767.9.
An International Search Report and a Written Opinion both dated Oct. 18, 2011, which issued during the prosecution of Applicant's PCT/IL2011/000222.
An International Preliminary Report on Patentability dated Sep. 11, 2012, which issued during the prosecution of Applicant's PCT/IL2011/000222.
An Office Action dated Mar. 16, 2017, which issued during the prosecution of Chinese Patent Application No. 201410483767.9.
An Office Action dated Jun. 25, 2015, which issued during the prosecution of U.S. Appl. No. 13/583,634.
An Office Action dated Apr. 3, 2015, which issued during the prosecution of Japanese Patent Application No. 2012-556642.
An Office Action dated Sep. 16, 2016, which issued during the prosecution of Japanese Patent Application No. 2015-175589.
An Office Action dated Feb. 11, 2015, which issued during the prosecution of Chinese Patent Application No. 2011/0013002.9.
An Office Action dated Aug. 4, 2014, which issued during the prosecution of Chinese Patent Application No. 2011/0013002.9.
An Office Action dated Feb. 22, 2017, which issued during the prosecution of U.S. Appl. No. 13/583,634.
An Office Action dated Apr. 4, 2014, which issued during the prosecution of U.S. Appl. No. 13/583,634.
An Office Action dated Nov. 5, 2014, which issued during the prosecution of U.S. Appl. No. 13/583,634.
An Office Action dated Jun. 14, 2016, which issued during the prosecution of U.S. Appl. No. 13/583,634.
Notice of Allowance dated May 28, 2015, which issued during the prosecution of No. 2011/0013002.9.
An Office Action dated May 24, 2016, which issued during the prosecution of Chinese Patent Application No. 201510483997.5.
An Office Action dated Jul. 20, 2016, which issued during the prosecution of Chinese Patent Application No. 201510483785.7.
An Office Action dated May 24, 2017, which issued during the prosecution of Chinese Patent Application No. 201510483785.7.
An Office Action dated Jun. 3, 2016, which issued during the prosecution of Chinese Patent Application No. 201410484557.1.
An Office Action dated Mar. 15, 2017, which issued during the prosecution of Chinese Patent Application No. 201410484557.1.
An Office Action dated Jun. 1, 2016, which issued during the prosecution of Chinese Patent Application No. 201510484559.0.
An Office Action dated Mar. 20, 2017, which issued during the prosecution of Chinese Patent Application No. 201510483997.5.
An Office Action dated Mar. 20, 2017, which issued during the prosecution of Chinese Patent Application No. 201510484559.0.
An Office Action dated Apr. 25, 2016, which issued during the prosecution of Chinese Patent Application No. 201510484558.6.
Notice of Allowance dated Mar. 10, 2017, which issued during the prosecution of Chinese Patent Application No. 201510484558.6.
An International Search Report and a Written Opinion both dated Jul. 13, 2012, which issued during the prosecution of Applicant's PCT/IL12/00003.
An International Preliminary Report on Patentability dated Sep. 10, 2013, which issued during the prosecution of Applicant's PCT/IL12/00003.
An Office Action dated Mar. 13, 2017, which issued during the prosecution of Chinese Patent Application No. 201510484566.0.
An Office Action dated Apr. 25, 2016, which issued during the prosecution of Chinese Patent Application No. 201510484566.0.
An Office Action dated Feb. 1, 2016, which issued during the prosecution of Australian Patent Application No. 2011225671.
Notice of Allowance dated Feb. 10, 2017, which issued during the prosecution Australian Patent Application No. 2011225671.
Single Balloon Endoscope: Balloon pump control OBCU: http://medical.olympusamerica.com/products/control/ballooncontrol-unit-obcu,[online].
Single Balloon Endoscope: SIF-Q 1 80 enteroscope: http://medical.olympusamerica.com/products/enteroscope/evisexera-ii-sif-q180,[online].
An Office Action dated Jan. 21, 2016, which issued during the prosecution of Canadian Patent Application No. 2,791,838.
European Search Report of Applicant's European dated Jul. 16, 2014, which issued during the prosecution App No. 12754885.7.
EVIS EXERA II CLV-180 product brochure, http://www.olympus.nl/medical/en/medical_systems/hidden/downloadJsp.jsp?link=/medical/rmt/media/content/content 1/documents 1/brochures 1/EVIS_EXERA_11_CLV-180_product_brochure_001_V1-en_GB 20000101.pdf, [online].
BS-2 Front Balloon, http://www.fujifilmusa.com/products/medical/endoscopy/endoscopes/specialized-balloons-andovertube/index.html#balloonsspecifications, [online].
An Office Action dated Jan. 30, 2017, which issued during the prosecution of Canadian Patent Application No. 2,791,838.
Double Balloon Endoscope: EC-450B15 colonoscope: http://www.fujifilmusa.com/products/medical/endoscopy/endoscopes/enteroscopes/index.html, [online].
Double Balloon Endoscope: Balloon pump controller BP-30: http://www.fujifilmusa.com/products/medical/endoscopy/endoscopes/balloon-pump-controller/index.html,[online].
Double Balloon Endoscope: EPX-4440HD video system: http://www.fujifilmusa.com/products/medical/endoscopy/video-systems/epx-4440hd, [online].
Double Balloon Endoscope: TS-13 101 overtube: http://www.fujifilmusa.com/products/medical/endoscopy/endoscopes/ specialized-balloons-and-overtube/index.html, [online].
Single Balloon Endoscope: ST-SB 1 overtube: http://medical.olympusamerica.com/products/tubes/single-use-st-sb11, [online].
U.S. Appl. No. 61/855,688, filed May 21, 2013.
U.S. Appl. No. 61/962,383, filed Nov. 6, 2013.
A communication from the European Patent Office dated Jul. 23, 2015, which issued during prosecution of European Application No. 12754885.7.
An Office Action dated Nov. 22, 2016, which issued during the prosecution of U.S. Appl. No. 13/583,634.
An Office Action dated Mar. 18, 2015, which issued during the prosecution of U.S. Appl. No. 13/583,634.
An Office Action dated May 9, 2016, which issued during the prosecution of U.S. Appl. No. 13/583,634.
An Office Action dated Oct. 7, 2015, which issued during the prosecution of U.S. Appl. No. 13/583,634.
An Office Action dated Mar. 28, 2017, which issued during the prosecution of U.S. Appl. No. 13/583,634.
A communication from the European Patent Office dated Jul. 6, 2016, which issued during the prosecution of European Application No. 12754885.7.
A communication from the European Patent Office dated May 17, 2017, which issued during the prosecution of European Application No. 12754885.7.
An Office Action dated Apr. 15, 2016, which issued during the prosecution of Chinese Patent Application No. 201280022024.6.
An Office Action dated May 26, 2015, which issued during the prosecution of Chinese Patent Application No. 201280022024.6.
An Office Action dated Nov. 1, 2016, which issued during the prosecution of Chinese Patent Application No. 201280022024.6.
An Office Action dated Dec. 9, 2016, which issued during the prosecution of Australian Patent Application No. 2012226390.
Notice of Allowance dated Dec. 22, 2016, which issued during the Patent Application No. 2012226390.
An Office Action dated Oct. 27, 2015, which issued during the prosecution of Japanese Patent Application No. 2013-557219.
An Office Action dated Oct. 24, 2016, which issued during the prosecution of Japanese Patent Application No. 2013-557219.
An Office Action dated Dec. 28, 2015, which issued during the prosecution of Japanese Patent Application No. 2015-004799.
An Office Action dated Dec. 6, 2016, which issued during the prosecution of Japanese Patent Application No. 2015-004799.

(56) References Cited

OTHER PUBLICATIONS

An Office Action dated Dec. 15, 2015, which issued during the prosecution of Australian Patent Application No. 2012226390.
An Office Action dated Sep. 3, 2015, which issued during the prosecution of Israel Patent Application No. 221621.
An Office Action dated Nov. 14, 2016, which issued during the prosecution of Israel Patent Application No. 228174.
An Office Action dated Jul. 5, 2017,. which issued during the prosecution of Chinese Patent Application No. 201280022024.6.
An Office Action dated Jul. 18, 2017, which issued during the prosecution of Canadian Patent Application No. 2,828,608.
An Office Action dated Jul. 24, 2017, which issued during the prosecution of Japanese Patent Application No. 2012-556642.
A Notice of Allowance dated Aug. 24, 2017, which issued during the prosecution of Chinese Patent Application No. 201510484557.1.
An Office Action dated Sep. 18, 2017, which issued during the prosecution of U.S. Appl. No. 14/891,683.
Office Action in JP 2016189043 dated Jul. 24, 2017.
Office Action in EP 11752941.2 dated Feb. 6, 2018.
Office Action in U.S. Appl. No. 14/003,799 dated Oct. 5, 2017.
Office Action in U.S. Appl. No. 14/003,799 dated Mar. 27, 2018.
Office Action in JP 2017012628 dated Feb. 26, 2018.
Office Action in JP 2016514529 dated Feb. 9, 2018.
Notice of Allowance in Chinese Patent App. No. 201510483785.7, dated Sep. 26, 2017.
Office Action in Chinese Patent App. No. 201510484566.0, dated Oct. 20, 2017.
Notice of Allowance in Chinese Patent App. No. 201510484557.1, dated Aug. 24, 2017.
Office Action in Chinese Patent App. No. 201510483767.9, dated Nov. 27, 2017.
Office Action in Chinese Patent App. No. 201510484559.0, dated Dec. 14, 2017.
Decision of Rejection in Chinese Patent App. No. 201510483997.5, dated Sep. 28, 2017.
Office Action in Chinese Patent App. No. 201480029252.5, dated Nov. 1, 2017.
Office Action in Australian Patent App. No. 2014269901, dated Jan. 12, 2018.
Office Action in Australian Patent App. No. 2017202285, dated Jan. 4, 2018.
Office Action in Canadian Patent App. No. 2,791,838, dated Dec. 15, 2017.
Final Rejection in U.S. Appl. No. 14/003,799, dated Oct. 5, 2017.
Non Final Rejection in U.S. Appl. No. 14/891,683, dated Sep. 18, 2017.
International Preliminary Report on Patentability in WO/2016/157189 dated Oct. 3, 2017.
International Search Report in WO/2016/157189 dated Sep. 7, 2016.
Written Opinion of the International Search Authority in WO/2016/157189 dated Sep. 7, 2016.
International Search Report in WO/2016/103247 dated Mar. 17, 2016.
Written Opinion of the International Search Authority in WO/2016/103247 dated Mar. 17, 2016.
International Preliminary Report on Patentability in WO/2016/103247 dated Jun. 27, 2017.

* cited by examiner

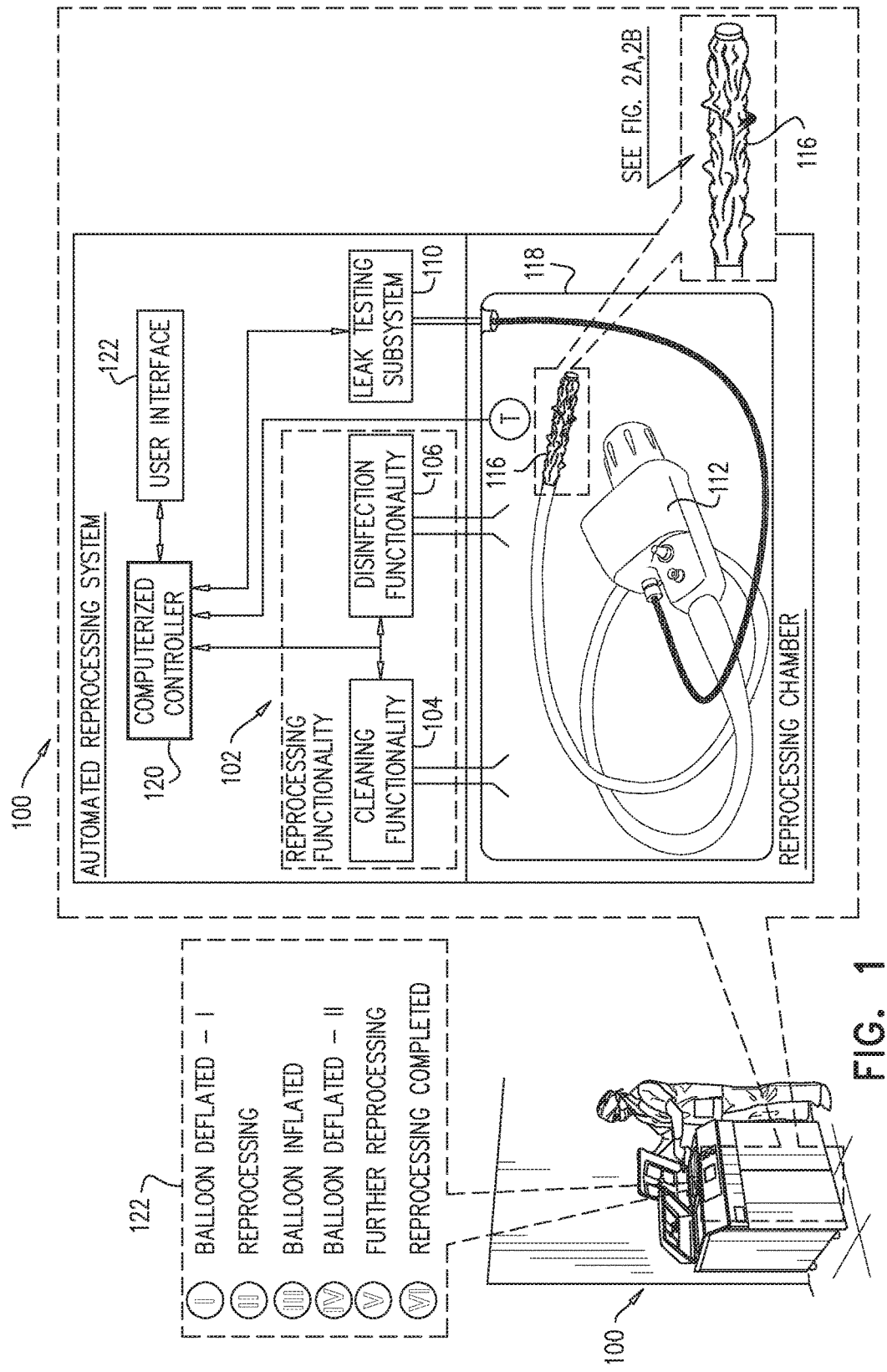

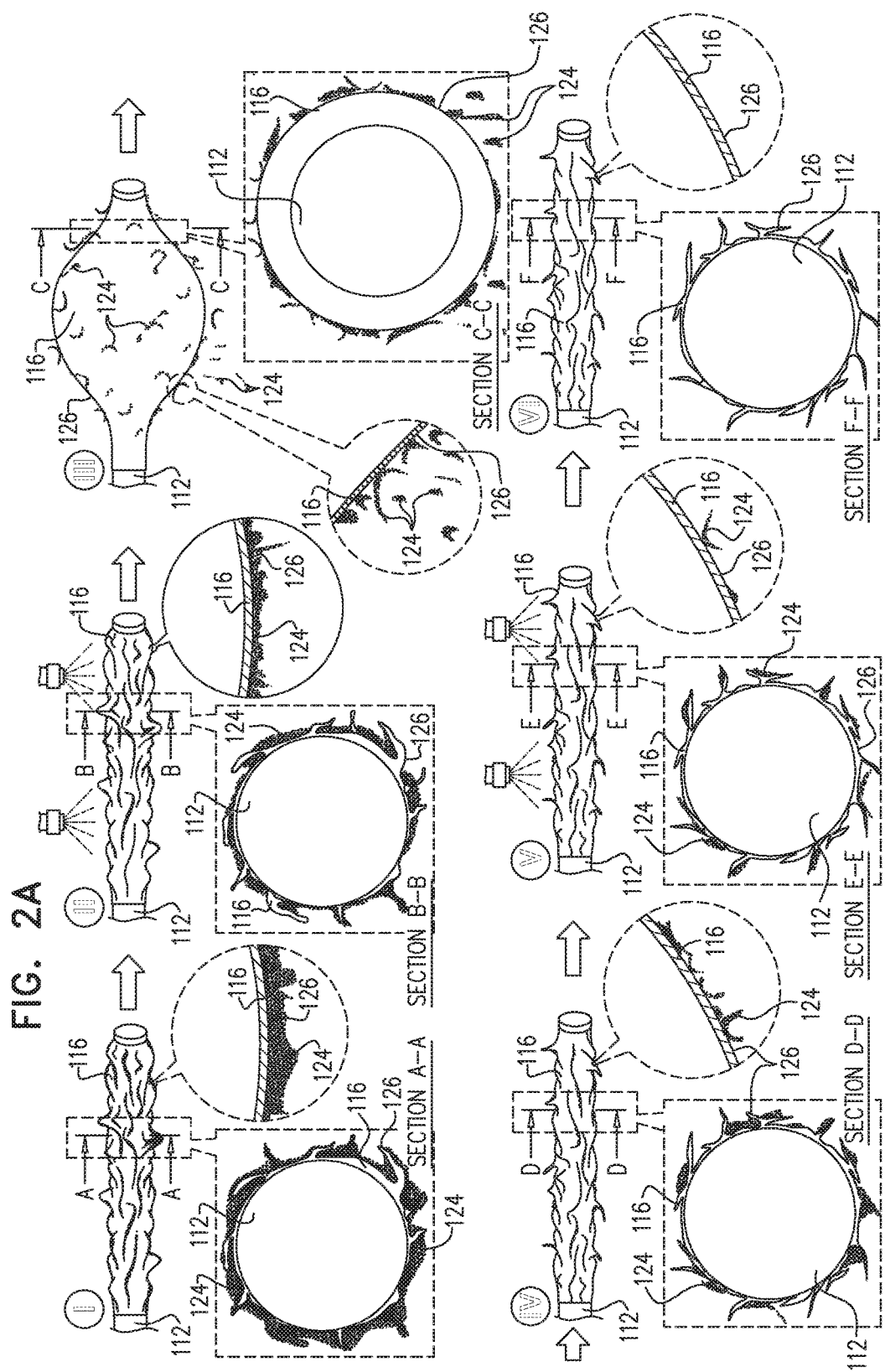

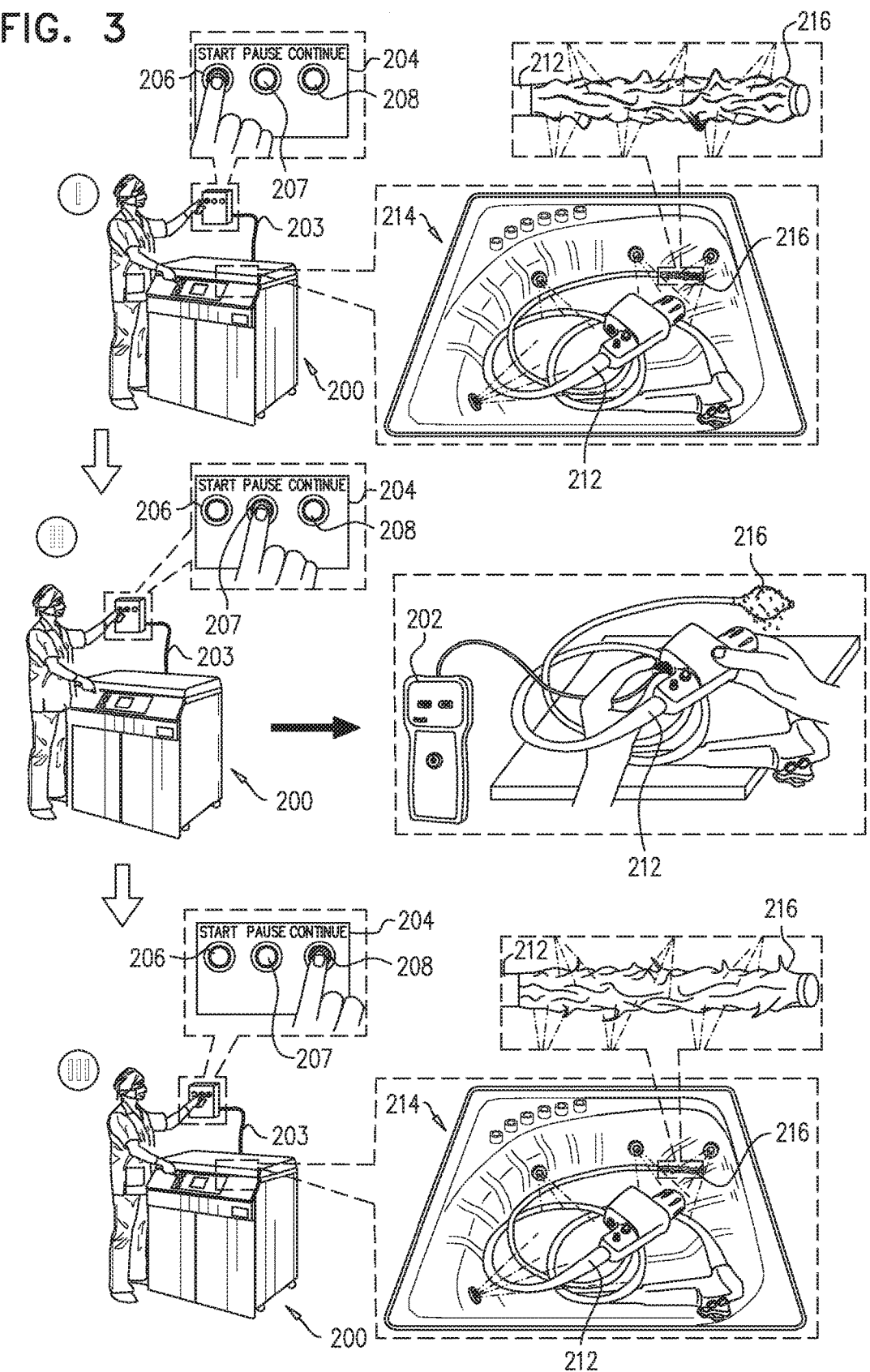

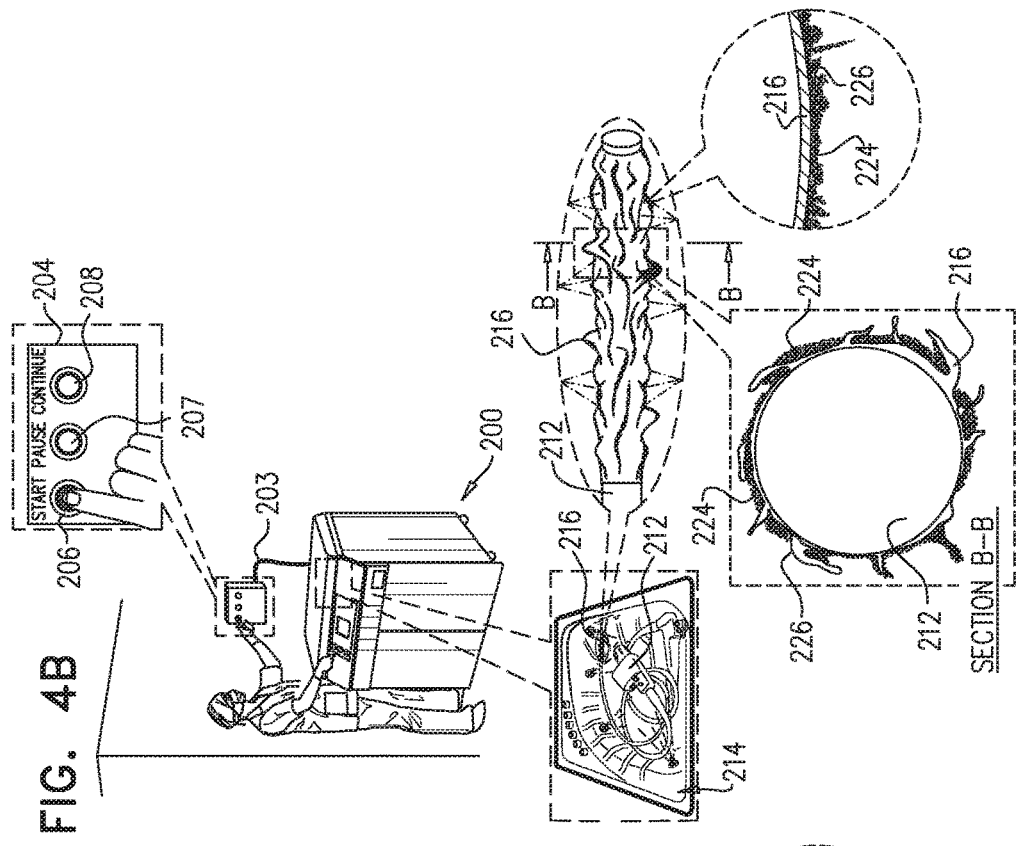
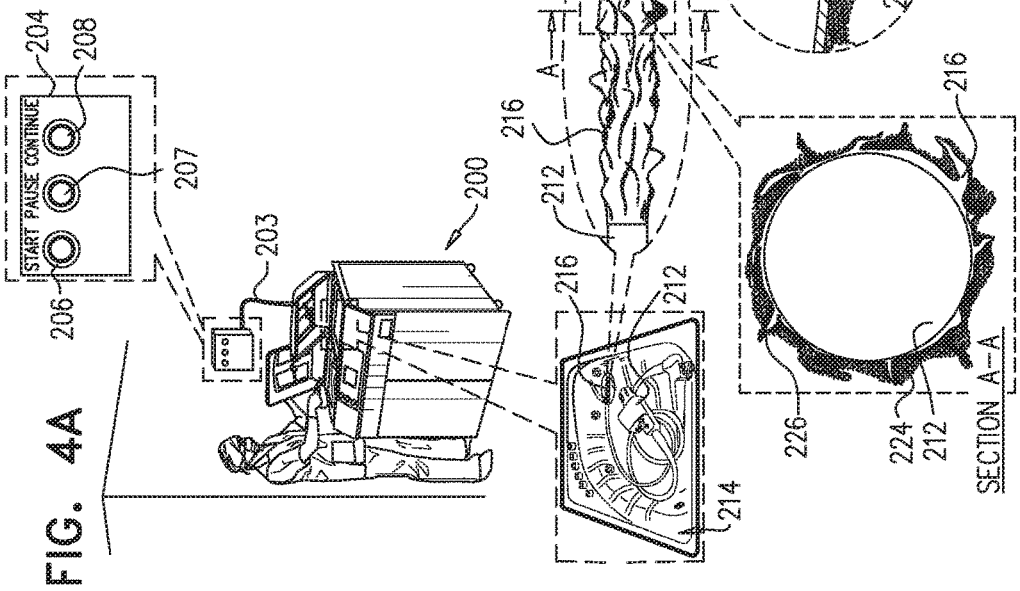

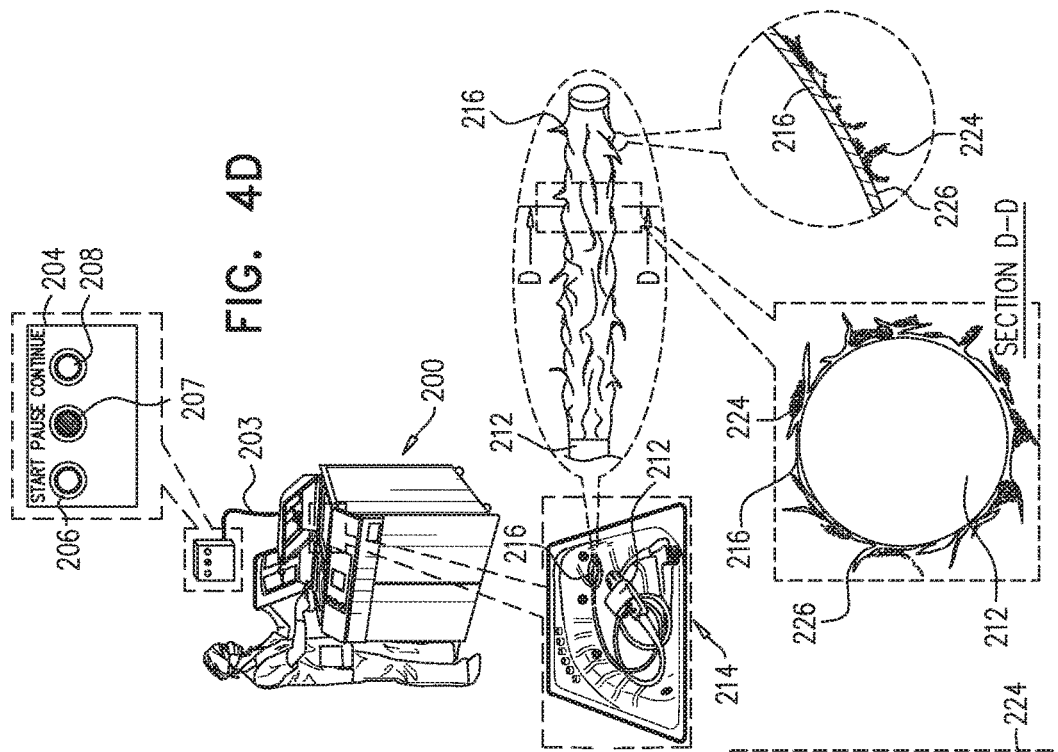
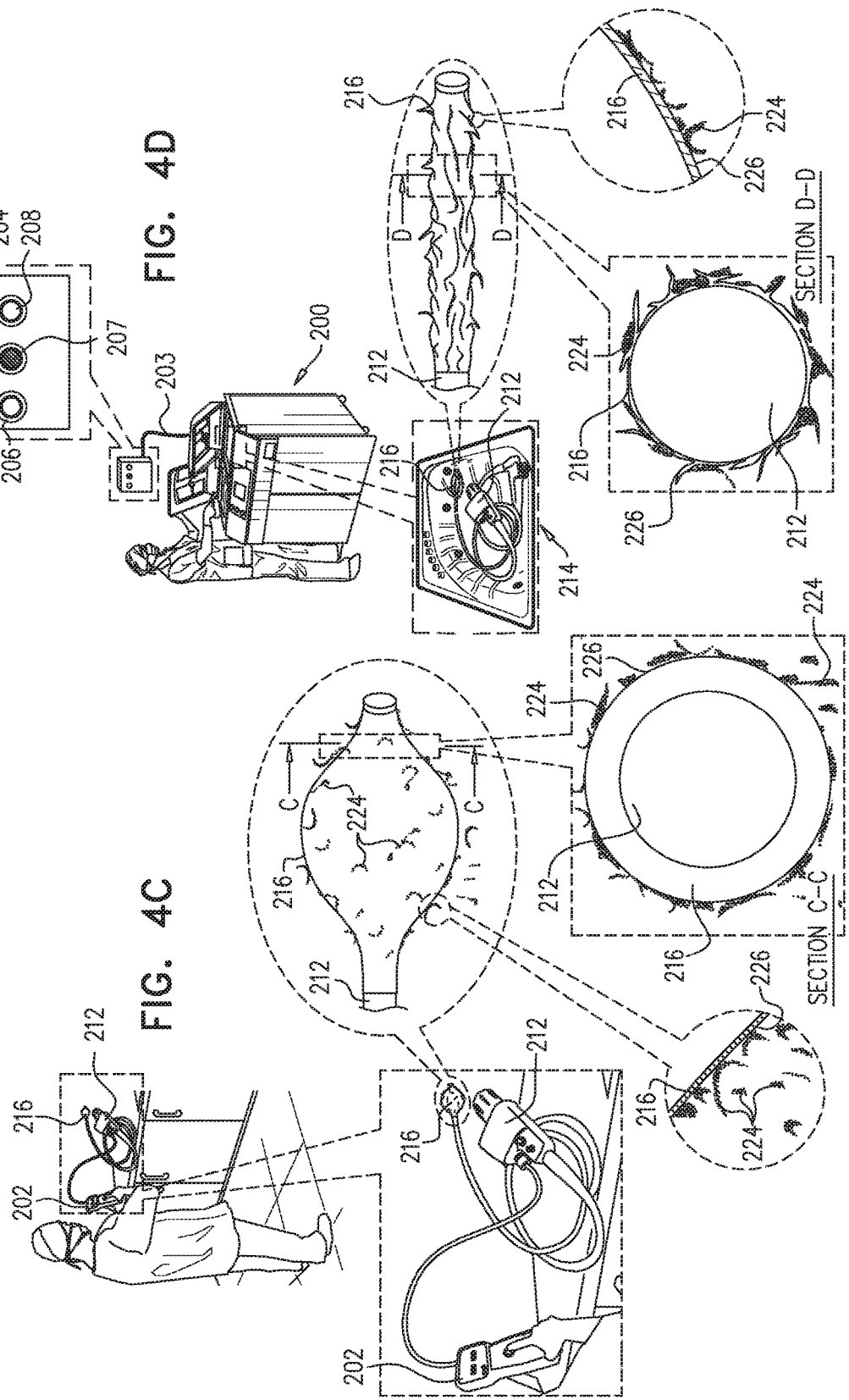

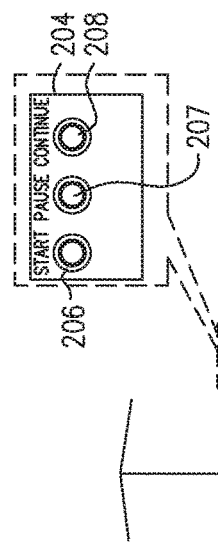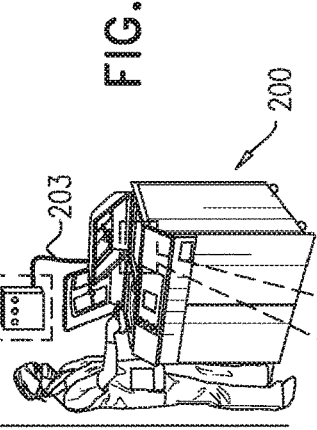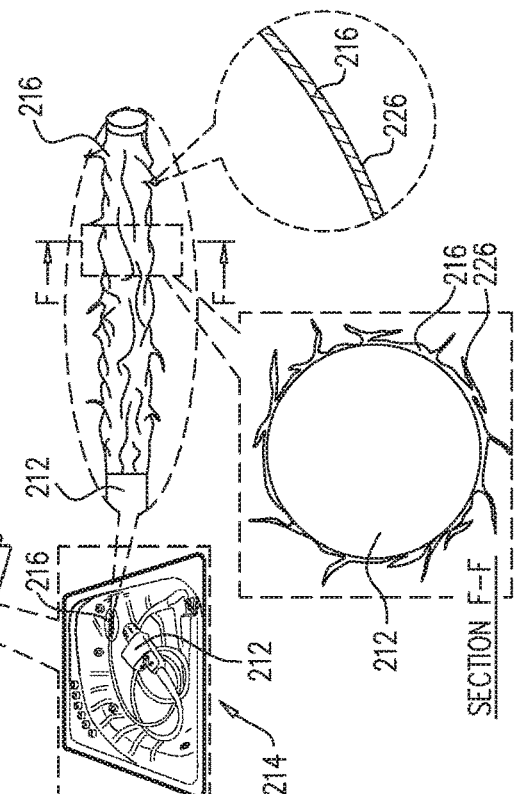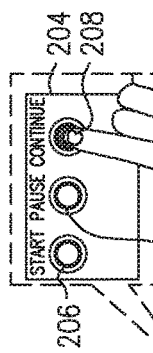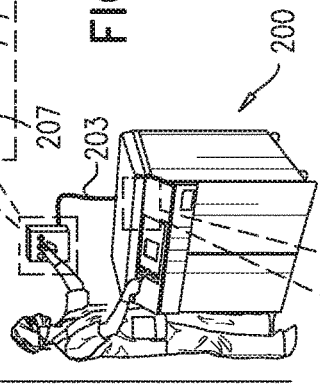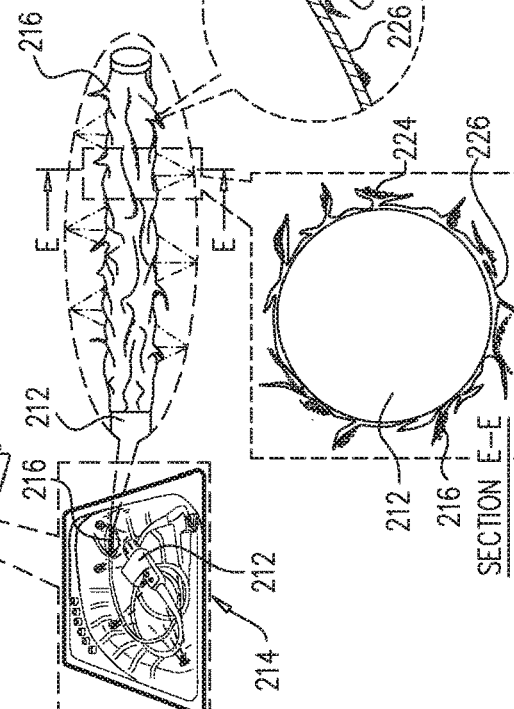
FIG. 4E
FIG. 4F

BALLOON ENDOSCOPE REPROCESSING SYSTEM AND METHOD

CROSS-REFERENCE TO RELATED APPLICATIONS

This application is a U.S. National Phase Application under 35 U.S.C. 371 of International Application No. PCT/IL2015/051149, which has an international filing date of Nov. 26, 2015, and which claims the priority benefit of U.S. Provisional Patent Application Ser. No. 62/124,551, filed on Dec. 22, 2014, and entitled "Endoscopic Reprocessing System Utilizing Negative and Positive Pressure Leak Testing," the disclosure of which is hereby incorporated by reference.

Reference is also made to applicant's Published PCT Patent Applications WO2005/074377; WO2007/017854; WO2007/135665; WO2008/004228; WO2008/142685; WO2009/122395; WO2010/046891; WO2010/137025; WO2011/111040; WO/2012/120492; WO/2014/068569 and WO2014/188402, the disclosures of which are hereby incorporated by reference.

FIELD OF THE INVENTION

The present invention relates to endoscope reprocessing methods and systems generally and more particularly to reprocessing of balloon endoscopes.

BACKGROUND OF THE INVENTION

Various types of methods and systems for reprocessing endoscopes are known.

SUMMARY OF THE INVENTION

The present invention seeks to provide improved methods and systems for reprocessing endoscopes.

There is thus provided in accordance with a preferred embodiment of the present invention a reprocessing method for balloon endoscopes, the method including introducing a balloon endoscope to be reprocessed into an endoscope reprocessing system, performing reprocessing on the balloon endoscope to be reprocessed while a balloon of the balloon endoscope is deflated, thereafter inflating the balloon of the balloon endoscope, thereafter deflating the balloon of the balloon endoscope and thereafter performing further reprocessing on the balloon endoscope to be reprocessed while the balloon of the balloon endoscope is deflated.

In accordance with a preferred embodiment of the present invention reprocessing is not performed on the balloon endoscope when the balloon is inflated. Alternatively, limited reprocessing is performed on the balloon endoscope when the balloon is inflated in a manner which does not damage the balloon. Additionally, the limited reprocessing includes at least one of the following procedures: pausing operation of moving parts in a reprocessing chamber of the endoscope reprocessing system, pausing heating of solutions used by the endoscope reprocessing system and monitoring and controlling pressure in the balloon to prevent over-inflation of the balloon.

In accordance with a preferred embodiment of the present invention the reprocessing method is carried out by the endoscope reprocessing system which includes a reprocessing controller which has at least the following operational stages: a first balloon endoscope balloon-deflated stage in which the balloon of the balloon endoscope is in a first balloon-deflated configuration, a reprocessing stage when the balloon of the balloon endoscope is in the first balloon-deflated configuration, a balloon-inflated stage in which the balloon of the balloon endoscope is in a balloon-inflated configuration, a further balloon-deflated stage following the balloon-inflated stage in which the balloon of the balloon endoscope is in a further balloon-deflated configuration and a further reprocessing stage when the balloon of the balloon endoscope is in the further balloon-deflated configuration.

In accordance with a preferred embodiment of the present invention the reprocessing method is carried out by the endoscope reprocessing system and a separate leak testing device and at least one of the thereafter inflating and the thereafter deflating is performed utilizing the separate leak testing device. More preferably, the reprocessing method is carried out by the endoscope reprocessing system and a separate leak testing device and the thereafter inflating and the thereafter deflating are performed utilizing the separate leak testing device.

Preferably, the reprocessing method for balloon endoscopes also includes removing the balloon endoscope from the reprocessing system subsequent to the performing reprocessing and replacing the balloon endoscope in the reprocessing system prior to the performing further reprocessing. Additionally, the reprocessing method for balloon endoscopes also includes pausing operation of the reprocessing system subsequent to the performing reprocessing and prior to the removing the balloon endoscope and restarting operation of the reprocessing system subsequent to the replacing the balloon endoscope.

In accordance with a preferred embodiment of the present invention during the performing reprocessing a first set of regions of an outer surface of the balloon of the balloon endoscope are exposed to reprocessing, during the performing further reprocessing a second set of regions of the outer surface of the balloon of the balloon endoscope are exposed to reprocessing and the first set of regions and the second set of regions are at least partially different. Additionally or alternatively, the performing reprocessing and the performing further reprocessing include performing an identical reprocessing step.

Preferably, the performing reprocessing on the balloon endoscope includes at least one of cleaning and disinfecting the balloon endoscope.

In accordance with a preferred embodiment of the present invention the thereafter deflating includes provision of negative pressure below −50 millibar in the balloon. More preferably, the thereafter deflating includes provision of negative pressure below −80 millibar in the balloon. Most preferably, the thereafter deflating includes provision of negative pressure below −100 millibar in the balloon.

In accordance with a preferred embodiment of the present invention the thereafter inflating includes provision of positive pressure in the range of 10 millibar to 120 millibar in the balloon. More preferably, the thereafter inflating includes provision of positive pressure in the range of 15 millibar to 70 millibar in the balloon. Even more preferably, the thereafter inflating includes provision of positive pressure in the range of 20 millibar to 60 millibar in the balloon.

In accordance with a preferred embodiment of the present invention the thereafter inflating includes provision of positive pressure below 80 millibar in the balloon.

There is also provided in accordance with another preferred embodiment of the present invention a reprocessing system for balloon endoscopes including a reprocessing chamber, an endoscope reprocessing subsystem, including cleaning functionality and disinfection functionality, and a leak testing subsystem including inflation and deflation functionality, the inflation and deflation functionality being operative to selectably inflate and deflate a balloon of the balloon endoscope while the balloon endoscope is located within the reprocessing chamber.

In accordance with a preferred embodiment of the present invention the reprocessing system for balloon endoscopes also includes a reprocessing controller operative to provide at least the following operational stages: a first balloon endoscope balloon-deflated stage in which a balloon of the balloon endoscope is in a first balloon-deflated configuration, a reprocessing stage when the balloon of the balloon endoscope is in the first balloon-deflated configuration, a balloon-inflated stage in which the balloon of the balloon endoscope is in a balloon-inflated configuration, a further balloon-deflated stage following the balloon-inflated stage in which the balloon of the balloon endoscope is in a further balloon-deflated configuration and a further reprocessing stage when the balloon of the balloon endoscope is in the further balloon-deflated configuration. Additionally, in the first balloon endoscope balloon-deflated configuration a first set of regions of an outer surface of a balloon of the balloon endoscope are exposed to reprocessing, in the second balloon endoscope balloon-deflated configuration a second set of regions of the outer surface of the balloon of the balloon endoscope are exposed to reprocessing and the first set of regions and the second set of regions are at least partially different.

Preferably, operation of the endoscope reprocessing subsystem in the first balloon endoscope reprocessing stage is identical to operation of the endoscope reprocessing subsystem in the second balloon endoscope reprocessing stage. Preferably, the endoscope reprocessing subsystem is only operative when a balloon of the balloon endoscope is in a deflated configuration. Alternatively, the reprocessing controller is operative to provide a limited reprocessing stage in which the balloon of the balloon endoscope is in the balloon-inflated configuration.

In accordance with a preferred embodiment of the present invention the reprocessing system includes at least one of the following elements: a leak testing subsystem including a vacuum/pressure pump and a vacuum/pressure sensor and being operative to provide positive and negative pressure to the balloon of the balloon endoscope and software embedded in the reprocessing controller of the reprocessing system, the software being operative to provide at least one of the following: control of a leak testing subsystem of the reprocessing system to maintain the balloon endoscope in a balloon-deflated configuration during reprocessing, provide at least two reprocessing stages, control of inflation and deflation of the balloon during the reprocessing, pause the operation of revolving jets and other moving parts in the reprocessing chamber during inflation of the balloon and cease heating of cleaning and/or disinfection solution during inflation of the balloon.

Preferably, the leak testing subsystem is operative to provide negative pressure below −50 millibar in the balloon. More preferably, the leak testing subsystem is operative to provide negative pressure below −80 millibar in the balloon. Most preferably, the leak testing subsystem is operative to provide negative pressure below −100 millibar in the balloon.

In accordance with a preferred embodiment of the present invention the leak testing subsystem is operative to provide positive pressure in the range of 10 millibar to 120 millibar in the balloon. More preferably, the leak testing subsystem is operative to provide positive pressure in the range of 15 millibar to 70 millibar in the balloon. Even more preferably, the leak testing subsystem is operative to provide positive pressure in the range of 20 millibar to 60 millibar in the balloon.

In accordance with a preferred embodiment of the present invention the leak testing subsystem is operative to provide positive pressure below 80 millibar in the balloon.

There is further provided in accordance with yet another preferred embodiment of the present invention a reprocessing system for balloon endoscopes including an endoscope reprocessing system, including cleaning functionality and disinfection functionality, and a leak testing device including inflation and deflation functionality, the inflation and deflation functionality being operative to selectably inflate and deflate a balloon of a balloon endoscope.

In accordance with a preferred embodiment of the present invention the reprocessing system provides at least the following operational stages: a first balloon endoscope balloon-deflated stage in which a balloon of the balloon endoscope is in a first balloon-deflated configuration, a reprocessing stage when the balloon of the balloon endoscope is in the first balloon-deflated configuration, a balloon-inflated stage in which the balloon of the balloon endoscope is in a balloon-inflated configuration, a further balloon-deflated stage following the balloon-inflated stage in which the balloon of the balloon endoscope is in a further balloon-deflated configuration and a further reprocessing stage when the balloon of the balloon endoscope is in the further balloon-deflated configuration.

Preferably, in the first balloon endoscope balloon-deflated configuration a first set of regions of an outer surface of a balloon of the balloon endoscope are exposed to reprocessing, in the second balloon endoscope balloon-deflated configuration a second set of regions of the outer surface of the balloon of the balloon endoscope are exposed to reprocessing and the first set of regions and the second set of regions are at least partially different. Additionally or alternatively, operation of the endoscope reprocessing system in the first balloon endoscope reprocessing stage is identical to operation of the endoscope reprocessing system in the second balloon endoscope reprocessing stage.

In accordance with a preferred embodiment of the present invention the leak testing device is operative to inflate and deflate the balloon of the balloon endoscope following removal of the balloon endoscope from the reprocessing system after reprocessing and prior to placement of the balloon endoscope in the reprocessing system for further reprocessing.

In accordance with a preferred embodiment of the present invention the endoscope reprocessing system is only operative when the balloon of the balloon endoscope is in a deflated configuration.

Preferably, the reprocessing stage includes at least one of cleaning and disinfection of the balloon endoscope.

In accordance with a preferred embodiment of the present invention the leak testing device is operative to provide negative pressure below −50 millibar in the balloon. More preferably, the leak testing device is operative to provide negative pressure below −80 millibar in the balloon. Even more preferably, the leak testing device is operative to provide negative pressure below −100 millibar in the balloon.

In accordance with a preferred embodiment of the present invention the leak testing device is operative to provide positive pressure in the range of 10 millibar to 120 millibar in the balloon. More preferably, the leak testing device is operative to provide positive pressure in the range of 15 millibar to 70 millibar in the balloon. Most preferably, the leak testing device is operative to provide positive pressure in the range of 20 millibar to 60 millibar in the balloon.

In accordance with a preferred embodiment of the present invention the leak testing device is operative to provide positive pressure below 80 millibar in the balloon.

BRIEF DESCRIPTION OF PREFERRED EMBODIMENTS

The present invention will be understood and appreciated more fully from the following detailed description, taken in conjunction with the drawings in which:

FIG. 1 is a simplified illustration of a balloon endoscope reprocessing system and the operation thereof in accordance with a preferred embodiment of the present invention;

FIGS. 2A and 2B are simplified illustrations of steps in two alternative embodiments of a balloon endoscope reprocessing method preferably employing the system of FIG. 1;

FIG. 3 is a simplified illustration of a balloon endoscope reprocessing system and the operation thereof in accordance with another preferred embodiment of the present invention; and FIGS. 4A, 4B, 4C, 4D, 4E and 4F are simplified illustrations of stages in a balloon endoscope reprocessing method preferably employing the system of FIG. 3.

DETAILED DESCRIPTION OF PREFERRED EMBODIMENTS

Figure 2B:
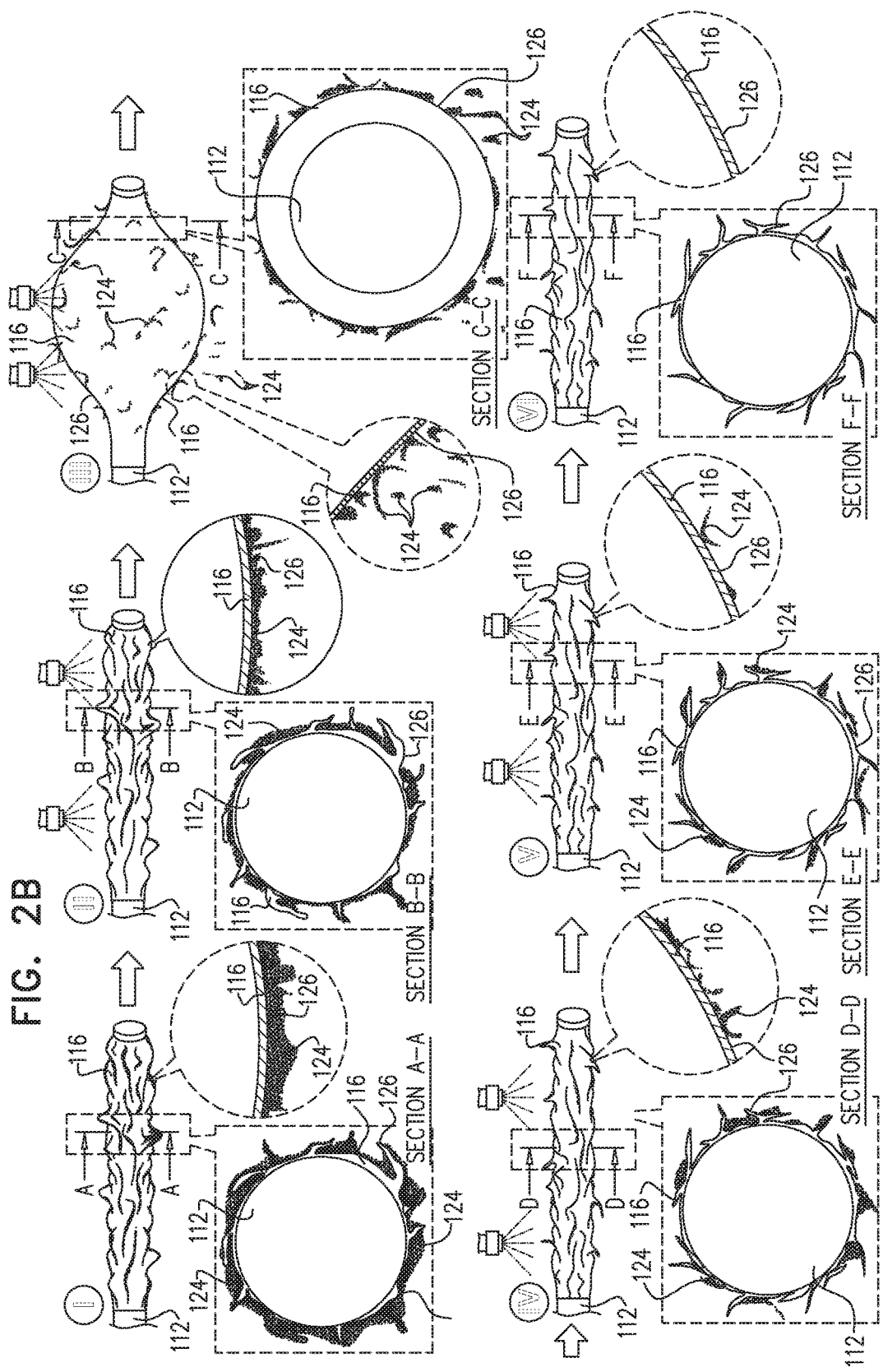

Reference is now made to FIG. 1, which is a simplified illustration of a balloon endoscope reprocessing system and the operation thereof in accordance with a preferred embodiment of the present invention, and to FIGS. 2A and 2B, which are simplified illustrations of steps in two alternative embodiments of a balloon endoscope reprocessing method preferably employing the system of FIG. 1.

In accordance with an embodiment of the present invention, a conventional endoscope reprocessing system is modified to enable the reprocessing system to carry out the steps of the embodiments of the methods illustrated in FIGS. 2A and 2B. Any suitable conventional endoscope reprocessing system may be modified in accordance with an embodiment of the present invention. Conventional reprocessing systems include, for example, model WASSENBURG® WD440 Endoscope Washer Disinfector, commercially available from Wassenburg Medical Devices B.V. of Edisonring 9, 6669 NA, Dodewaard, the Netherlands, model MEDIVATORS® ADVANTAGE® Plus Endoscope Washer Disinfector, commercially available from MEDIVATORS Inc., of 14605 28th Avenue North, Minneapolis, Minn. 55447 USA, and model Olympus® ETD3® Endoscope Washer Disinfector, commercially available from Olympus Europe GmbH, of Wendenstrasse 14-18, 20097, Hamburg, Germany.

The modified endoscope reprocessing system, here generally designated by reference numeral 100, preferably includes generally all of the conventional reprocessing functionality 102 of the conventional endoscope reprocessing system, including cleaning functionality 104 and disinfection functionality 106, as well as an added or modified leak testing subsystem 110. The leak testing subsystem 110 is shown in FIG. 1 coupled to a balloon endoscope 112 to be reprocessed, having an inflatable and deflatable balloon 116, such as a G-EYE™ 3890i colonoscope, commercially available from Smart Medical Systems, of 10 Hayetsira street, Raanana, Israel, which is located within a reprocessing chamber 118 of the reprocessing system 100.

It is a particular feature of the embodiments of the present invention shown in FIGS. 2A & 2B that the reprocessing functionality 102, including cleaning functionality 104 and disinfection functionality 106, and the leak testing subsystem 110 are controlled by a modified reprocessing computerized controller 120, which is preferably operated by a user interface 122 to have at least the following operational stages:

a first balloon endoscope balloon-deflated stage in which a balloon of the balloon endoscope is in a first balloon-deflated configuration;

a reprocessing stage when the balloon of the balloon endoscope is in the first balloon-deflated configuration;

a balloon-inflated stage in which the balloon of the balloon endoscope is in a balloon-inflated configuration;

a further balloon-deflated stage following the balloon-inflated stage in which the balloon of the balloon endoscope is in a further balloon-deflated configuration; and a further reprocessing stage when the balloon of the balloon endoscope is in the further balloon-deflated configuration.

FIGS. 1, 2A and 2B each illustrate the following six sequential operational stages:
I—balloon deflated
II—reprocessing when balloon deflated
III—balloon inflated
IV—balloon deflated
V—further reprocessing when balloon deflated
VI—reprocessing completed From a consideration of FIGS. 2A and 2B, it can be seen that the balloon 116 is deflated at all stages other than stage III. It is also seen by comparing the enlargements in stages I and II that the amount of biological residues and fecal matter 124 on the outer surface 126 of the balloon 116 is reduced by the reprocessing stage II. It is further seen by considering the enlargement in stage III, that inflation and subsequent redeflation of balloon 116 preferably has two positive effects:

enhanced separation of biological residues and fecal matter 124 from the outer surface of the balloon; and arrangement of the folds of the balloon 116, when redeflated, in an arrangement different from that when the balloon 116 was earlier deflated (Stage I), such that different regions of the outer surface 126 are exposed to cleaning and disinfection.

Comparing the embodiments of FIGS. 2A and 2B, it is seen that in the embodiment illustrated in FIG. 2A, the balloon endoscope is reprocessed only when the balloon 116 is deflated and the balloon is inflated and subsequently deflated between two reprocessing stages, which reprocessing stages may or may not be identical. This embodiment, which involves inflation and repeated deflation, has a distinct advantage in that it exposes different surfaces of the deflated balloon 116 and thus produces enhanced cleaning of the balloon in reprocessing, as well as enhanced disinfection of the balloon in reprocessing.

It is appreciated that reprocessing the balloon endoscope only when it is in a balloon-deflated configuration has the advantage of preventing mechanical damage to balloon 116 during reprocessing, such as rupture by revolving jets of the reprocessing system 100, when reprocessing system 100 employs revolving jets, over-inflation of balloon 116 due to air expansion at elevated reprocessing temperatures which may result in irreversible distortion of balloon 116, and other adverse consequences.

The reprocessing method of this embodiment of the present invention may thus be summarized as including at least the following steps:

introducing a balloon endoscope to be reprocessed into an endoscope reprocessing system;

performing reprocessing on the balloon endoscope to be reprocessed while a balloon of the balloon endoscope is deflated;

thereafter inflating the balloon of the balloon endoscope;

thereafter deflating the balloon of the balloon endoscope; and thereafter performing further reprocessing on the balloon endoscope to be reprocessed while the balloon of the balloon endoscope is deflated.

It is appreciated that additional stages of balloon inflation and subsequent deflation followed by additional reprocessing stages when the balloon 116 is in a deflated configuration may be provided as appropriate to achieve a desired quality of reprocessing.

In contrast to the above-described embodiment shown in FIG. 2A, in the embodiment of FIG. 2B, a limited reprocessing operation may take place while the balloon is inflated, as illustrated in stage III in FIG. 2B. In this embodiment, the reprocessing system operates continuously prior to, during, and after, the inflation and subsequent redeflation of balloon 116.

With reference to FIGS. 1 and 2B, according to this embodiment the first portion of the reprocessing operation, which is referred to as REPROCESSING and is denoted as stage II in FIG. 1, is carried out prior to and during the inflation and subsequent deflation of balloon 116, throughout stages II, III and IV shown in FIG. 2B, and the second portion of the reprocessing operation which is carried out after redeflation of balloon 116 is referred to as FURTHER REPROCESSING and is denoted as stage V in FIGS. 1 and 2B. In this embodiment as well, this inflation and deflation has a distinct advantage in that it exposes different surfaces of the deflated balloon 116 and thus produces enhanced cleaning of the balloon in reprocessing as well as enhanced disinfection of the balloon in reprocessing.

The reprocessing method of the embodiment of the present invention illustrated in FIG. 2B may thus be summarized as including at least the following steps:

introducing a balloon endoscope to be reprocessed into an endoscope reprocessing system;

performing reprocessing on the balloon endoscope to be reprocessed while a balloon of the balloon endoscope is deflated;

thereafter inflating the balloon of the balloon endoscope;

thereafter deflating the balloon of the balloon endoscope; and thereafter performing further reprocessing on the balloon endoscope to be reprocessed while the balloon of the balloon endoscope is deflated.

It is appreciated that additional stages of balloon inflation and subsequent deflation followed by additional reprocessing stages may be provided as appropriate to achieve a desired quality of reprocessing.

It is appreciated that inflating the balloon 116 while the balloon endoscope is being reprocessed has the advantages of saving time and simplifying the reprocessing operation, however, it is appreciated that the reprocessing performed while balloon 116 is inflated is preferably a limited reprocessing and is preferably performed for a short period of time during which the cleaning functionality 104, the disinfection functionality 106, and the leak testing subsystem 110 are operated in a limited reprocessing mode to prevent mechanical damage to the inflated balloon 116 during reprocessing.

In particular, the operation of revolving jets or other moving parts in the reprocessing chamber 118, to the extent such are employed by the cleaning functionality 104 and/or disinfection functionality 106, is preferably paused when the balloon 116 is being inflated, to prevent rupture of the inflated balloon 116.

Furthermore, heating of cleaning or disinfection solutions by the cleaning functionality 104 and/or disinfection functionality 106, is preferably paused when the balloon 116 is being inflated, to prevent over-inflation of balloon 116 due to air expansion at elevated reprocessing temperatures which may result in irreversible distortion of balloon 116. Additionally or alternatively, pressure in balloon 116 is continuously controlled and monitored by leak testing subsystem 110 during inflation of balloon 116, to prevent over-inflation and resulting irreversible distortion of the inflated balloon 116.

It is appreciated that the balloon-deflated configuration of balloon endoscope 112 is achieved by provision to balloon 116 of negative pressure, namely pressure lower than the ambient pressure (which is typically atmospheric pressure), by leak testing subsystem 110. Preferably, the negative pressure in balloon 116 is below −50 millibar (meaning that the atmospheric pressure is higher than the absolute pressure in the balloon 116 by more than 50 millibar). More preferably, the negative pressure in balloon 116 is below −80 millibar. Yet more preferably, the negative pressure in balloon 116 is below −100 millibar.

It is further appreciated that the balloon-inflated configuration of balloon endoscope 112 is achieved by provision to balloon 116 of positive pressure, namely pressure higher than the ambient pressure (which is typically atmospheric pressure), by leak testing subsystem 110. Preferably, the positive pressure in balloon 116 is in the range of 10 millibar to 120 millibar (meaning that the absolute pressure in balloon 116 is higher than the atmospheric pressure by 10-120 millibar). More preferably, the positive pressure in balloon 116 is in the range of 15 millibar to 70 millibar. Yet more preferably, the positive pressure in balloon 116 is in the range of 20 millibar to 60 millibar. In accordance with another embodiment of the invention, the positive pressure in the inflated balloon 116 is below 80 millibar.

It is appreciated that the modified conventional reprocessing system 100 includes one or more of the following modifications of the conventional reprocessing system, as required for enabling it to perform the reprocessing method of the invention as described with respect to the embodiments of FIGS. 1, 2A and 2B:

addition of a vacuum/pressure pump and a vacuum/pressure sensor to leak testing subsystem 110 for provision of positive and negative pressure to balloon 116 of balloon endoscope 112 during inflation and deflation of balloon 116, and for maintenance of negative pressure in balloon 116 during reprocessing;

modification of the software embedded in the modified reprocessing computerized controller 120 to control the leak testing subsystem 110 to maintain the balloon endoscope 112 in a balloon-deflated configuration during reprocessing;

modification of the software embedded in the modified computerized controller 120 to provide reprocessing and further reprocessing instead of a single, continuous reprocessing operation;

modification of the software embedded in the modified computerized controller 120 to effect inflation and deflation of balloon 116 during the reprocessing operation; and modification of the software embedded in the modified reprocessing computerized controller 120 to provide a limited reprocessing mode during inflation of balloon 116, which limited reprocessing mode may include at least one of:

pausing the operation of revolving jets and other moving parts in the reprocessing chamber 118;

controlling and monitoring the pressure in balloon 116 to prevent over-inflation; and pausing heating of cleaning and/or disinfection solution.

It is a particular feature of the invention, as described with respect to the embodiments of FIGS. 1, 2A and 2B, that the balloon 116 of balloon endoscope 112 is in a balloon-deflated configuration throughout most or all of the reprocessing operation, and that the balloon 116 is inflated following part of the reprocessing operation for a short period of time, typically shorter than 3 minutes, and is then redeflated. Preferably, the balloon 116 is maintained by the modified endoscope reprocessing system 100 in a balloon-inflated configuration for a time period shorter than 1 minute. More preferably, the balloon 116 is maintained by the modified endoscope reprocessing system 100 in a balloon-inflated configuration for a time period in the range of 1-50 seconds. Yet more preferably, the balloon 116 is maintained by the modified endoscope reprocessing system 100 in a balloon-inflated configuration for a time period in the range of 1-30 seconds. In the context of the present invention a balloon-inflated configuration is a configuration in which the pressure inside the balloon is higher than the ambient pressure (which it typically the atmospheric pressure).

Reference is now made to FIG. 3, which is a simplified illustration of a balloon endoscope reprocessing system and the operation thereof in accordance with another preferred embodiment of the invention, and to FIGS. 4A, 4B, 4C, 4D, 4E and 4F, which are simplified illustrations of stages in a balloon endoscope reprocessing method preferably employing the system of FIG. 3.

It is a particular feature of this embodiment of the present invention that the reprocessing method is carried out by a conventional endoscope reprocessing system and a separate leak testing device, wherein at least one and preferably both, inflating and deflating the balloon is carried out by a separate leak testing device.

As seen in FIGS. 3 and 4A-4F, in an embodiment of the present invention, a conventional endoscope reprocessing system 200 and a separate conventional leak testing device 202 are employed in order to carry out the steps of the method of FIGS. 4A-4F. Any suitable conventional endoscope reprocessing system may be employed in accordance with this embodiment of the present invention. Conventional reprocessing systems include, for example, model WASSENBURG® WD440 Endoscope Washer Disinfector, commercially available from Wassenburg Medical Devices B.V. of Edisonring 9, 6669 NA, Dodewaard, the Netherlands, model MEDIVATORS® ADVANTAGE® Plus Endoscope Washer Disinfector, commercially available from MEDIVATORS Inc., of 14605 28th Avenue North, Minneapolis, Minn. 55447 U.S.A, and model Olympus® ETD3® Endoscope Washer Disinfector, commercially available from Olympus Europe GmbH, of Wendenstrasse 14-18, 20097, Hamburg, Germany. The leak testing device 202 may be a G-EYE™ Leak Tester Device commercially available from Smart Medical Systems, of 10 Hayetsira street, Raanana, Israel.

Preferably, the power cord 203 of conventional endoscope reprocessing system 200 is connected to mains electrical power via a switch 204, which preferably has three operation buttons, a START button 206, a PAUSE button 207, and a CONTINUE button 208. START button 206 is effective, when pressed, to provide electrical power to reprocessing system 200 and to terminate the supply of electrical power to reprocessing system 200 when subsequently pressed again. PAUSE button 207 is operative, when pressed, to interrupt the supply of electrical power to reprocessing system 200 without causing electrical spikes that may damage reprocessing system 200 and CONTINUE button 208 is operative when pressed to release PAUSE button 207 and resume the supply of electrical power to reprocessing system 200.

It is appreciated that some or all of the functions of buttons 206, 207 and 208 may be available on the user interface of conventional endoscope reprocessing system 200, and may be operated therethrough instead of by pressing the buttons of switch 204. It is appreciated that if the functions of all three buttons of the switch 204, START, PAUSE and CONTINUE, can be performed by the existing functionalities and user interface of the conventional reprocessing system 200, the switch 204 may be obviated and the power cord 203 of reprocessing system 200 may be connected directly to a mains electrical power outlet.

As seen in FIGS. 3 and 4A, a balloon endoscope 212, such as a G-EYE™ 3890i colonoscope, commercially available from Smart Medical Systems, of 10 Hayetsira street, Raanana, Israel, is located within a reprocessing chamber 214 of the reprocessing system 200. As further seen in FIGS. 3 and 4A-4F, the balloon endoscope 212 is not coupled to a leak testing subsystem of conventional reprocessing system 200, to the extent that the conventional reprocessing system 200 includes such a leak testing subsystem. At this stage, an inflatable and deflatable balloon 216 of balloon endoscope 212 is in a balloon-deflated configuration. The reprocessing system 200 is operated in a normal mode of operation to carry out an initial reprocessing step, by pressing the START button 206 of the switch 204, and/or by pressing a power-on button of the conventional reprocessing system 200, to provide electrical power to reprocessing system 200.

It is a particular feature of this embodiment of the present invention that the conventional reprocessing system 200 and the separate conventional leak testing device 202 are preferably operated to have at least the following six sequential operational stages, which are illustrated in FIGS. 4A-4F:

A. balloon deflated
B. reprocessing when balloon is deflated
C. balloon inflated
D. balloon deflated
E. further reprocessing when balloon is deflated
F. reprocessing completed From a consideration of FIGS. 3 and 4A-4F, it can be seen that the balloon 216 is deflated in all stages other than stage C (as seen in stage II in FIG. 3 and in FIG. 4C). It is also appreciated that the amount of biological residues and fecal matter 224 on the outer surface 226 of the balloon 216 is reduced by the reprocessing stage B (FIG. 4B). It is further seen by considering the enlargement in FIGS. 4C and 4D, that inflation and subsequent redeflation of balloon 216 preferably has two positive effects:

enhanced separation of fecal matter 224 from the outer surface 226 of the balloon; and arrangement of the folds of the balloon 216, when redeflated, in an arrangement different from that when the balloon 216 was earlier deflated (Stage I), such that different regions of the outer surface 226 are exposed to cleaning and disinfection.

It is thus appreciated that in accordance with a preferred embodiment of the invention the balloon endoscope 212 is only reprocessed when the balloon 216 is deflated and the balloon 216 is inflated and subsequently deflated between two reprocessing stages, which stages may or may not be identical. This inflation and deflation has a distinct advantage in that it exposes different surfaces of the deflated balloon 216 and thus produces enhanced cleaning of the balloon 216 in reprocessing.

The reprocessing method of this embodiment of the present invention may thus be summarized as including at least the following steps:

introducing a balloon endoscope 212 to be reprocessed into a conventional endoscope reprocessing system 200, as seen in FIG. 4A;

ensuring that the balloon endoscope 212 to be reprocessed is in a first balloon-deflated configuration, as seen in FIGS. 4A and 4B;

performing reprocessing on the balloon endoscope 212 to be reprocessed in the first balloon-deflated configuration by pressing the START button 206 on the switch 204 and/or by pressing an appropriate button of the reprocessing system 200, as seen in FIG. 3 at stage I and in FIG. 4B;

causing the balloon endoscope 212 to assume a balloon-inflated configuration, preferably by removing the balloon endoscope 212 from the conventional endoscope reprocessing system 200 following pressing of the PAUSE button 207 on switch 204 or by pressing an appropriate pause or stop button of the conventional reprocessing system 200, and connecting the balloon endoscope to the conventional leak testing device 202 which is then operated to inflate the balloon 216, as seen in FIG. 3 at stage II and in FIG. 4C;

thereafter causing the balloon endoscope 212 to assume a second balloon-deflated configuration, preferably using the conventional leak testing device 202 for balloon deflation and disconnecting balloon endoscope 212 from the leak testing device 202 and reinserting it into the reprocessing chamber 214 of the conventional reprocessing system 200 following deflation of balloon 216; and thereafter performing further reprocessing on the balloon endoscope 212 to be reprocessed in the second balloon-deflated configuration, by pressing the CONTINUE button 208 on switch 204 or by pressing an appropriate resume or start button of the conventional reprocessing system 200, as seen in FIG. 3 at stage III and in FIGS. 4D-4E.

It is appreciated that additional stages of balloon inflation and subsequent deflation followed by additional reprocessing stages may be provided as appropriate to achieve a desired quality of reprocessing.

It is appreciated that balloon inflation and deflation may be performed by any suitable device other than the conventional leak testing device 202, for example by using a balloon inflation/deflation device, such as a NaviAid SPARK2C inflation system, commercially available from Smart Medical Systems, of 10 Hayetsira street, Raanana, Israel.

It is appreciated that the balloon-deflated configuration of balloon endoscope 212 is achieved by provision to balloon 216 of negative pressure, namely pressure lower than the ambient pressure (which is typically atmospheric pressure), preferably by the leak testing device 202.

Preferably, the negative pressure in balloon 216 is below −50 millibar (meaning that the atmospheric pressure is higher than the absolute pressure in the balloon 216 by more than 50 millibar). More preferably, the negative pressure in balloon 216 is below −80 millibar. Yet more preferably, the negative pressure in balloon 216 is below −100 millibar.

It is further appreciated that the balloon-inflated configuration of balloon endoscope 212 is achieved by provision to balloon 216 of positive pressure, namely pressure higher than the ambient pressure (which is typically atmospheric pressure), preferably by the leak testing device 202.

Preferably, the positive pressure in balloon 216 is in the range of 10 millibar to 120 millibar (meaning that the absolute pressure in balloon 216 is higher than the atmospheric pressure by 10-120 millibar). More preferably, the positive pressure in balloon 216 is in the range of 15 millibar to 70 millibar. Yet more preferably, the positive pressure in balloon 216 is in the range of 20 millibar to 60 millibar. In accordance with another embodiment of the invention, the positive pressure in the inflated balloon 216 is below 80 millibar.

It is a particular feature of the embodiment of FIGS. 3 and 4A-4F, that the balloon 216 of balloon endoscope 212 is in a balloon-deflated configuration throughout the entire reprocessing operation, and that the balloon 216 is inflated following part of the reprocessing operation for a short period of time throughout which it is not reprocessed, typically shorter than 3 minutes, and is then redeflated. Preferably, the balloon 216 is maintained in a balloon-inflated configuration for a time period shorter than 1 minute. More preferably, the balloon 216 is maintained in a balloon-inflated configuration for a time period in the range of 1-50 seconds. Yet more preferably, the balloon 216 is maintained in a balloon-inflated configuration for a time period in the range of 1-30 seconds. It is appreciated that balloon-inflated configuration is a configuration in which the pressure inside the balloon is higher than the ambient pressure (which it typically the atmospheric pressure).

It is appreciated that performance of all or substantially all of the reprocessing operation while the balloon endoscope 212 is in a balloon-deflated configuration as described with respect to the embodiment of FIGS. 3 and 4A-4F, has the advantage of preventing mechanical damage to balloon 216 during reprocessing, such as rupture by revolving jets of the reprocessing system 200, over-inflation of balloon 216 due to air expansion at elevated reprocessing temperatures which may result in irreversible distortion of balloon 216, and other adverse consequences.

It is a particular purpose of the present invention, as seen in all embodiments described hereinabove, to provide a reprocessing method for balloon endoscopes that includes reprocessing in two balloon-deflated configurations of the balloon endoscope being reprocessed, wherein in the first balloon-deflated configuration, a first set of regions of an outer surface of a balloon of the balloon endoscope are exposed to reprocessing, in said second balloon-deflated configuration, a second set of regions of said outer surface of said balloon of said balloon endoscope are exposed to reprocessing, and wherein the first set of regions and the second set of regions are at least partially different. It is appreciated that reprocessing of the balloon endoscope preferably includes at least one of cleaning and disinfection of the balloon endoscope.

It will be appreciated by persons skilled in the art that the present invention is not limited by what has been particularly shown and described hereinabove. Rather the scope of the present invention includes both combinations and sub-combinations of features described and illustrated as well as modifications and variations thereof which are not in the prior art.

The invention claimed is:

1. A reprocessing method for balloon endoscopes, the method comprising:
   introducing a balloon endoscope to be reprocessed into an endoscope reprocessing system;
   performing reprocessing on said balloon endoscope to be reprocessed while a balloon of said balloon endoscope is deflated;
   thereafter inflating said balloon of said balloon endoscope;
   thereafter deflating said balloon of said balloon endoscope; and
   thereafter performing further reprocessing on said balloon endoscope to be reprocessed while said balloon of said balloon endoscope is deflated.

2. A reprocessing method for balloon endoscopes according to claim 1 and wherein reprocessing is not performed on said balloon endoscope when said balloon is inflated.

3. A reprocessing method for balloon endoscopes according to claim 1 and wherein said reprocessing method is carried out by said endoscope reprocessing system which includes a reprocessing controller which has at least the following operational stages:
   a first balloon endoscope balloon-deflated stage in which said balloon of the balloon endoscope is in a first balloon-deflated configuration;
   a reprocessing stage when the balloon of the balloon endoscope is in the first balloon-deflated configuration;
   a balloon-inflated stage in which the balloon of the balloon endoscope is in a balloon-inflated configuration;
   a further balloon-deflated stage following the balloon-inflated stage in which the balloon of the balloon endoscope is in a further balloon-deflated configuration; and
   a further reprocessing stage when the balloon of the balloon endoscope is in the further balloon-deflated configuration.

4. A reprocessing method for balloon endoscopes according to claim 1 and wherein:
   said reprocessing method is carried out by said endoscope reprocessing system and a separate leak testing device; and
   at least one of said thereafter inflating and said thereafter deflating is performed utilizing said separate leak testing device.

5. A reprocessing method for balloon endoscopes according to claim 4 and also comprising:
   removing said balloon endoscope from said reprocessing system subsequent to said performing reprocessing; and
   replacing said balloon endoscope in said reprocessing system prior to said performing further reprocessing.

6. A reprocessing method for balloon endoscopes according to claim 5 and also comprising:
   pausing operation of said reprocessing system subsequent to said performing reprocessing and prior to said removing said balloon endoscope; and
   restarting operation of said reprocessing system subsequent to said replacing said balloon endoscope.

7. A reprocessing system for balloon endoscopes comprising:
   a reprocessing chamber;
   an endoscope reprocessing subsystem including:
      cleaning functionality; and
      disinfection functionality;
   a leak testing subsystem including inflation and deflation functionality, said inflation and deflation functionality being operative to selectably inflate and deflate a balloon of said balloon endoscope while said balloon endoscope is located within said reprocessing chamber; and
   a reprocessing controller operative to provide at least the following operational stages:
      a first balloon endoscope balloon-deflated stage in which a balloon of the balloon endoscope is in a first balloon-deflated configuration,
      a reprocessing stage when the balloon of the balloon endoscope is in the first balloon-deflated configuration,
      a balloon-inflated stage in which the balloon of the balloon endoscope is in a balloon-inflated configuration,
      a further balloon-deflated stage following the balloon-inflated stage in which the balloon of the balloon endoscope is in a further balloon-deflated configuration, and
      a further reprocessing stage when the balloon of the balloon endoscope is in the further balloon-deflated configuration.

8. A reprocessing system for balloon endoscopes according to claim 7 and wherein:
   in said first balloon endoscope balloon-deflated configuration a first set of regions of an outer surface of a balloon of said balloon endoscope are exposed to reprocessing;
   in said second balloon endoscope balloon-deflated configuration a second set of regions of said outer surface of said balloon of said balloon endoscope are exposed to reprocessing; and
   said first set of regions and said second set of regions are at least partially different.

9. A reprocessing system for balloon endoscopes according to claim 7 and wherein operation of said endoscope reprocessing subsystem in said first balloon endoscope reprocessing stage is identical to operation of said endoscope reprocessing subsystem in said second balloon endoscope reprocessing stage.

10. A reprocessing system for balloon endoscopes according to 7 and wherein said endoscope reprocessing subsystem is only operative when a balloon of said balloon endoscope is in a deflated configuration.

11. A reprocessing system for balloon endoscopes according to 7 and wherein said reprocessing controller is operative to provide a limited reprocessing stage in which said balloon of said balloon endoscope is in said balloon-inflated configuration.

12. A reprocessing system for balloon endoscopes according to 7 and wherein said reprocessing system comprises at least one of the following elements:
   a leak testing subsystem comprising a vacuum/pressure pump and a vacuum/pressure sensor and being operative to provide positive and negative pressure to said balloon of said balloon endoscope; and
   software embedded in said reprocessing controller of said reprocessing system, said software being operative to provide at least one of the following:

control of a leak testing subsystem of said reprocessing system to maintain the balloon endoscope in a balloon-deflated configuration during reprocessing;

provide at least two reprocessing stages;

control of inflation and deflation of said balloon during said reprocessing;

pause the operation of revolving jets and other moving parts in said reprocessing chamber during inflation of said balloon; and cease heating of cleaning and/or disinfection solution during inflation of said balloon.

13. A reprocessing system for balloon endoscopes according to claim 12 and wherein said leak testing subsystem is operative to provide negative pressure below −50 millibar in said balloon.

14. A reprocessing system for balloon endoscopes according to claim 12 and wherein said leak testing subsystem is operative to provide negative pressure below −80 millibar in said balloon.

15. A reprocessing system for balloon endoscopes according to claim 12 and wherein said leak testing subsystem is operative to provide negative pressure below −100 millibar in said balloon.

16. A reprocessing system for balloon endoscopes according to claim 12 and wherein said leak testing subsystem is operative to provide positive pressure in the range of 10 millibar to 120 millibar in said balloon.

17. A reprocessing system for balloon endoscopes according to claim 12 and wherein said leak testing subsystem is operative to provide positive pressure in the range of 15 millibar to 70 millibar in said balloon.

18. A reprocessing system for balloon endoscopes according to claim 12 and wherein said leak testing subsystem is operative to provide positive pressure in the range of 20 millibar to 60 millibar in said balloon.

19. A reprocessing system for balloon endoscopes according to claim 12 and wherein said leak testing subsystem is operative to provide positive pressure below 80 millibar in said balloon.

* * * * *